(12) United States Patent
Pfaendler et al.

(10) Patent No.: US 7,247,622 B2
(45) Date of Patent: Jul. 24, 2007

(54) PHARMACEUTICAL COMPOSITIONS CONTAINING OXAPENEM-3-CARBOXYLIC ACIDS

(75) Inventors: Hans Rudolf Pfaendler, Stockdorp (DE); Iain Nelson Simpson, Harlton (GB)

(73) Assignee: Amura Limited, Cambridge (GB)

( * ) Notice: Subject to any disclaimer, the term of this patent is extended or adjusted under 35 U.S.C. 154(b) by 0 days.

(21) Appl. No.: 10/399,704

(22) PCT Filed: Oct. 11, 2001

(86) PCT No.: PCT/GB01/04527

§ 371 (c)(1),
(2), (4) Date: Jul. 24, 2003

(87) PCT Pub. No.: WO02/32423

PCT Pub. Date: Apr. 25, 2002

(65) Prior Publication Data
US 2004/0067929 A1    Apr. 8, 2004

(30) Foreign Application Priority Data
Oct. 19, 2000  (EP) ................................. 00309207
Mar. 8, 2001   (GB) ................................. 0105766.0
Aug. 6, 2001   (GB) ................................. 0119165.9

(51) Int. Cl.
C07D 503/14   (2006.01)
C07D 503/22   (2006.01)
A61K 31/424   (2006.01)
A61P 31/04    (2006.01)
(52) U.S. Cl. ................................. 514/210.06; 540/347
(58) Field of Classification Search ................ 540/347; 514/210.06
See application file for complete search history.

(56) References Cited

U.S. PATENT DOCUMENTS 4,293,555 A    10/1981  Christensen et al.

(Continued)

FOREIGN PATENT DOCUMENTS

EP    0 018 305 A1    10/1980

(Continued)

*Primary Examiner*—Mark L. Berch
(74) *Attorney, Agent, or Firm*—Edwards Angell Palmer & Dodge LLP; Kathleen M. Williams; Ralph A. Loren

(57) ABSTRACT

An oxapenem compound which is, or is capable of forming, a zwitterion of formula

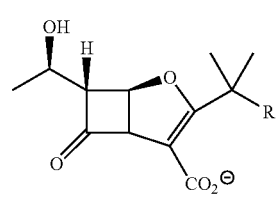

Ia

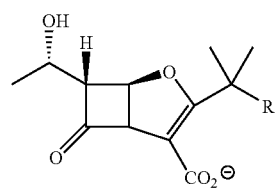

Ib wherein R is a $C_1$-$C_8$ branched or straight chain alkyl group which is substituted by a protonated nitrogen base. The compounds find particular use as high bio-availability β-lactamase inhibitors.

26 Claims, 2 Drawing Sheets

U.S. PATENT DOCUMENTS 5,108,747 A * 4/1992 Pfaendler et al. ........... 424/114
2004/0043980 A1* 3/2004 Pfaendler ............... 514/210.06
2004/0176349 A1* 9/2004 Simpson et al. ....... 514/210.06

FOREIGN PATENT DOCUMENTS

| EP | 0 301 394 A1 | 2/1989 |
| EP | 0 362 622 A1 | 4/1990 |
| EP | 0 474 038 A1 | 3/1992 |
| EP | 0 548 790 A1 | 6/1993 |
| EP | 548790 A1 * | 6/1993 |
| WO | WO 96/38448 A1 | 12/1996 |

* cited by examiner

PHARMACEUTICAL COMPOSITIONS CONTAINING OXAPENEM-3-CARBOXYLIC ACIDS

The present invention relates to oxapenem compounds, to pharmaceutical compositions containing them and to their medical uses.

β-lactam antibiotics (for example penicillins, cephalosporins and carbapenems) are well-known for treatment of bacterial infections, but their prolonged use is associated with increased bacterial resistance.

The principal mechanism of bacterial resistance is by β-lactamases. There are four classes of β-lactamase, known as classes A to D. Clinically, class A and class C β-lactamases are the most important. Combination therapy utilising a β-lactam antibiotic and a β-lactamase inhibitor has proven successful at counteracting some forms of resistance. Known combination products are, for example, Tazocim (RTM) which is a combination of piperacillin antibiotic and tazobactam inhibitor, and Augmentin (RTM), a combination of amoxycillin antibiotic and clavulanic acid inhibitor. However, tazobactam and clavulanic acid are only effective against class A β-lactamases, leaving their antibiotic partners unprotected against class B, D and, most importantly, class C β-lactamases.

Although β-lactamase inhibitors with activity against the class C β-lactamases are known, to date there is no commercially available "broad spectrum" inhibitor active against both class A and C β-lactamases.

EP 0 301394 discloses a wide variety of oxapenem compounds which are antibacterial agents. EP 0 362622 discloses oxapenem compounds which are broad spectrum β-lactamase inhibitors, highly active against class A, class C and class D β-lactamases. EP 0 548790 discloses that the stereochemistry of a chiral side chain on the 6-carbon of the oxapenem structure has a marked effect on in vitro β-lactamase inhibitory activity. Compounds having a (1'S)-1-hydroxylalkyl side chain, with opposite configuration to that of thienamycin, show increased in vitro activity against TEM 1 β-lactamase from *E. Coli,* a common class A β-lactamase. None of the above documents give evidence of particular in vivo activity.

It is also important to achieve sufficiently high blood levels and long biological half-lives of β-lactams to treat bacterial infections. With traditional β-lactam antibiotics, e.g in the Cephalosporin field this problem has been solved with compounds such as Ceftazidime and Ceftriaxon (in vivo biological half lifes in human serum 1.7-2.1 hrs and 5.8-8.7 hrs resp.). In contrast, the corresponding in vivo biological half-lives of non-traditional β-lactams, e.g. the carbapenems Imipenem and are much shorter (0.9 and 1.0 hrs). The in vivo half life of Clavulanate is (0.7-1.4 hrs). A relatively long biological half-life is very important for the practical applicability of antibiotics and β-lactamase inhibitors.

The present applicants have found that several novel compounds within the broadest generic disclosure of EP 0 362622 display surprisingly high bioavailability, and superior activity against class A and class C β-lactamases. Furthermore, they have found that they exhibit unexpected and superior stability in blood serum which may lead to increased blood levels and increased biological half life.

According to the present invention in a first aspect there is provided an oxapenem compound which is, or is capable of forming, a zwitterion of formula Ia or Ib:

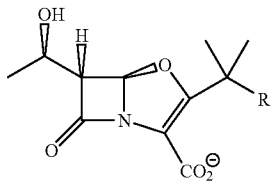

Ia

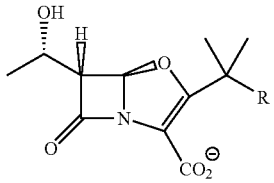

Ib wherein R is a $C_1$-$C_8$ branched or straight chain alkyl group which includes a protonated basic substituent.

Preferably the protonated basic substituent is a protonated nitrogen base. More preferably the protonated basic substituent is a protonated amine or protonated aminomethyleneamino substituent.

Preferred compounds are those of formula Ia wherein R is —$(CH_2)_4NH_3^+$ (hereinafter referred to as Compound E); R is —$(CH_2)_3NH_3^+$ (hereinafter referred to as Compound PFOB); R is —$(CH_2)_2NH_3^+$ (hereinafter referred to as Compound A); R is —$(CH_2)_2NHCH:NH_2^+$ (hereinafter referred to as Compound B); or R is —$CH_2NHCH:NH_2^+$ (hereinafter referred to as Compound D).

It will be appreciated that the protonation of Nitrogen in the R groups of B and D shown above can take place at either Nitrogen. Thus B and D may also be represented by formula Ia wherein R is —$(CH_2)_2NH_2^+CH:NH$ and —$CH_2NH_2^+CH:NH$.

Also preferred is the compound of formula Ib wherein R is —$(CH_2)_3NH_3^+$ (hereinafter referred to as YOB).

It will be appreciated that there is an equilibrium between the compounds of the invention in their zwitterionic form (i.e. when the basic (e.g. amine) group has been protonated and the carboxylic acid group deprotonated) and their "non ionic" form (when base (e.g. amine) and carboxylic acid groups are neutral). The "non ionic" forms of the compositions, and equilibrium mixtures of zwitterionic and "non ionic" forms, are all within the scope of the invention. Thus, "an oxapenem compound which is capable of forming a zwitterion" includes oxapenem compounds in the "non ionic" form, that is oxapenem compounds of Formula Ia or Formula Ib wherein the $CO_2^-$ has been protonated to $CO_2H$, and the "protonated basic group" or "protonated nitrogen base" on the R group has been deprotonated. Examples of oxapenem compounds which are capable of forming a zwitterion are compounds of Formula Ia wherein the $CO_2^-$ has been protonated to $CO_2H$ and the R groups are —$(CH_2)_4NH_2$, —$(CH_2)_3NH_2$, —$(CH_2)_2NH_2$, —$(CH_2)_2NHCH:NH$, or —$CH_2NHCH:NH$; and compounds of Formula Ib wherein the $CO_2^-$ has been protonated to $CO_2H$ and the R group is —$(CH_2)_3NH_2$.

Further, "an oxapenem compound which is capable of forming a zwitterion" also includes mixtures of the oxapenem compounds in both the zwitterionic and "non ionic" forms.

The applicants have found that the combination of: (a) particular stereochemistry at positions 5 and 6 of the oxapenem double ring structure; and (b) the particular zwitterionic structure (or the capability of being able to form such a zwitterionic structure); gives compounds with remarkable bioavailability and wide spectrum of activity.

The claimed compounds show remarkably high bioavailability compared to known compounds. The compounds show remarkable activity against class A and C β-lactamases. Compound YOB in particular shows remarkably high activity and selectivity against class A β-lactamases.

The compounds described in this invention and β-lactam antibiotics are active against a wide range of Gram-positive (staphylococci, streptococci) and Gram-negative (enterobacteriaceae, non-fermentative species) bacteria responsible for infections of the urinary tract, respiratory tract, wounds and intra-abdominal sepsis. The oxapenem compound and antibiotic may be administered concurrently (for example as a mixture), or, for example, as separate medicaments. The oxapenem and antibiotic may be administered at different times.

According to the invention in a further aspect there is provided a pharmaceutical composition comprising a pharmacologically effective amount of an oxapenem compound according to the first aspect of the invention. Preferred pharmaceutical compositions further comprise a pharmacologically effective amount of an antibiotic. The antibiotic may be a β-lactam antibiotic (e.g. ceftazidime).

According to the invention in a still further aspect there is provided a method of treatment of infection comprising a step of administering to a patient in need thereof a pharmacologically effective amount of a zwitterion of formula Ia or Ib:

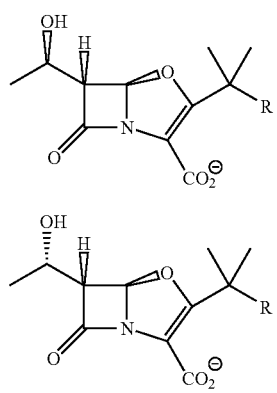

wherein R is a $C_1$-$C_8$ branched or straight chain alkyl group which includes a protonated basic substituent. Preferably the protonated basic substituent is a protonated nitrogen base. Preferably the protonated basic substituent is a protonated amine or protonated aminomethyleneamino substituent. The method may further comprise a step of administering to the patient a pharmacologically effective amount of an antibiotic. The oxapenem compound and antibiotic may be administered concurrently, or at different times.

The treatment may be by β-lactamase inhibition.

Preferably, the method is for treatment of infections of the urinary tract, respiratory tract, wounds and intra-abdominal sepsis. The patient may be a human or animal patient.

BRIEF DESCRIPTION OF THE DRAWINGS

The present invention will now be illustrated with reference to the drawings in which.

DETAILED DESCRIPTION OF THE INVENTION

Over 40 oxapenem analogues have been synthesised and tested in vitro. Structure activity relationship (SAR) studies have identified functions for various parts of the oxapenem molecule with respect to chemical stability, target binding affinity, antibacterial activity and spectrum and extent of β-lactamase inhibition. It has not been possible to predict bioavailability from structure studies.

We have synthesised and tested several oxapenem compounds, known as PFOB, YOB, A, E, B, D, U and XOB. Their structures are shown in Table 1. It can be seen that PFOB, YOB, E, B, D and A are embodiments of the present invention. The syntheses are discussed below.

TABLE 1

Structures of Oxapenem Compounds

| Compound | Formula | | R. Group |
|---|---|---|---|
| PFOB | (structure) | Ia | —$(CH_2)_3NH_3^+$ |
| | | Ib | |
| E | (structure) | Ia | —$(CH_2)_3NH_3^+$ |
| | | Ib | |
| A | (structure) | Ia | —$(CH_2)_3NH_3^+$ |
| | | Ib | |
| B | (structure) | Ia | $(CH_2)_2NHCH:NH_2^+$ |
| | | Ib | |

TABLE 1-continued

Structures of Oxapenem Compounds

| Compound | Formula | | R. Group |
|---|---|---|---|
| D | [structure] | Ia | —$CH_2NHCH:NH_2^+$ Ib |
| YOB | [structure] | Ib | —$(CH_2)_3NH_3^+$ Ib |
| U | [structure] | Ia | —$CH_3$ Ib |
| XOB | [structure] | Ib | —$CH_3$ |

A. Pharmacokinetic Testing

Figure 1:
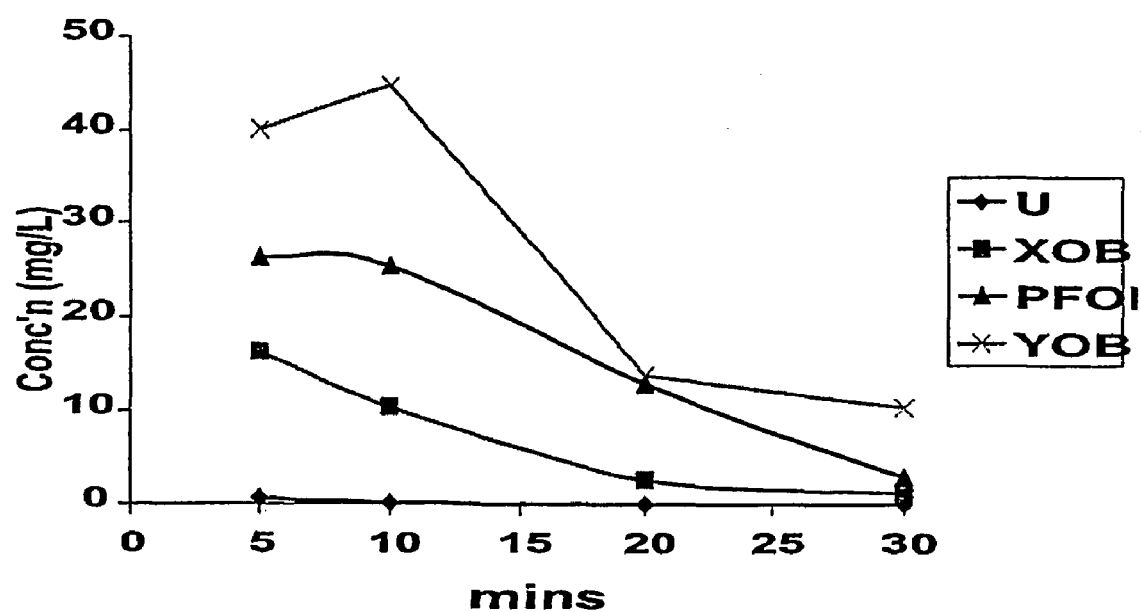
FIG. 1 shows plasma blood levels of oxapenem analogues following subcutaneous administration at 50 mg per kg in mice.

The plasma blood levels in mice (mean of 3 per time point) of compositions XOB, YOB, PFOB and YOB were measured at time points of 5, 10, 20 and 30 minutes following subcutaneous (SC) administration at a dose of 50 mg per kg. The results are shown in Table 2 and illustrated in FIG. 1.

TABLE 2

| Compound | Conc. (mg/L) 5 min | Conc. (mg/L) 10 min | Conc. (mg/L) 20 min | Conc. (mg/L) 30 min |
|---|---|---|---|---|
| YOB | 40.12 | 44.88 | 13.79 | 10.4 |
| PFOB | 26.42 | 25.39 | 12.9 | 2.89 |
| XOB | 16.2 | 10.43 | 2.63 | 1.21 |
| U | 0.55 | 0.21 | 0.03 | 0 |

It can be clearly seen from the plasma blood levels at all time points that following sub-cutaneous administration, the compounds of the invention (zwitterionic compounds PFOB and YOB) have remarkably superior bioavailability when compared with salts XOB and U. Further, it should be noted that the only difference between PFOB and U, and YOB and XOB, is the amine substituted chain (instead of methyl group) in compounds PFOB and YOB. The amine substituted chain allows the zwitterionic structure. Thus, the compositions are extremely suitable for use in hospitals in i.p. and s.c administration regimes.

B. In Vitro Activity in Combination with Ceftazidime

The assays to determine the Minimum Inhibitory Concentration (MIC) were performed by Agar dilution according to NCCLS guidelines (2000). In the following data the lowest MIC shows the strongest activity.

Class A β-lactamases

Ceftazidime alone (CAZ), and a 2:1 ratio of ceftazidime with each of PFOB, YOB, U and XOB (CAZ+PFOB, CAZ+YOB, CAZ+U and CAZ+XOB) were each tested against a variety of Class A β-lactamases. The results are shown in Table 3.

TABLE 3

Inhibitory Activity vs Class A β-lactamases

| Organism | CAZ | CAZ + PFOB | CAZ + YOB | CAZ + U | CAZ + XOB |
|---|---|---|---|---|---|
| E. coli ATCC 25922 | 0.25 | 0.25 | 0.03 | 0.125 | 0.25 |
| E. coli ATCC 35218 | 0.125 | 0.125 | 0.125 | 0.125 | 0.125 |
| E. coli J53-1 | 0.125 | 0.125 | 0.125 | 0.125 | 0.25 |
| E. coli TEM-1 | 0.25 | 0.5 | 0.06 | 0.25 | 0.25 |
| E. coli TEM-3 | 16 | 2 | 2 | 2 | 2 |
| E. coli TEM-6 | >64 | 4 | 2 | 8 | 2 |
| E. coli TEM-9 | >64 | 8 | 2 | 8 | 4 |
| E. coli TEM-10 | >64 | 16 | 2 | 8 | 4 |

It can be seen that against E. coli TEM-3, TEM-6, TEM-9 and TEM-10 all of the oxapenems, when used in combination with CAZ, show markedly superior activity compared to CAZ alone.

YOB, a composition according to the invention, shows remarkable activity when compared to XOB (a structurally and stereochemically close composition which is not a zwitterion). This is particularly well demonstrated by the MIC values against E. coli ATCC 25922 and TEM-1 for YOB (0.03 and 0.06) when compared to those for XOB (0.25 and 0.25). It is noted that the MIC values against TEM-9 and TEM-10 also show superiority.

Class C β-lactamases

Ceftazidime alone (CAZ), and a 1:1 ratio of ceftazidime with each of PFOB, YOB, U and XOB (CAZ+PFOB, CAZ+YOB, CAZ+U and CAZ+XOB) were each tested against a variety of Class C β-lactamases. The results are shown in table 4.1.

TABLE 4.1

Inhibitory Activity vs Enterobacteriaceae de-repressed Class C β-lactamases

| Organism | CAZ | CAZ + PFOB | CAZ + YOB | CAZ + U | CAZ + XOB |
|---|---|---|---|---|---|
| E. cloacae P99 | 32 | 4 | 4 | 2 | 4 |
| E. cloacae Hennessy | >64 | 4 | 16 | 4 | 4 |
| E. cloacae 84-CON | >64 | 4 | 8 | 8 | 8 |
| C. freundii C2-con | 64 | 0.03 | 4 | 2 | 2 |
| S marcescens S2-con | 1 | 0.03 | 0.03 | 0.25 | 0.5 |

It can be seen that against all organisms all of the oxapenems, when used in combination with CAZ, show superior activity compared to CAZ alone.

PFOB, a composition according to the invention, shows remarkable activity when compared to U (a structurally and stereochemically close composition which is not a zwitterion). This is demonstrated by the MIC values against *E. cloacae* 84-con, *C Freundii* C2-con and *S marcescens* S2-con for PFOB (4, 0.03 and 0.03, respectively) when compared to those for U (8, 2 and 0.25). It is also noted that the MIC value for YOB against *S marcescens* S2-con is markedly superior to that of XOB.

Ceftazidime alone (CAZ), and a 2:1 ratio of ceftazidime with each of PFOB, YOB, U and XOB (CAZ+PFOB, CAZ+YOB, CAZ+U and CAZ+XOB) were each tested against a variety of Class C β-lactamases. The results are shown in table 4.2.

TABLE 4.1

Inhibitory Activity vs Enterobacteriaceae derepressed Class C β-lactamases (Ratio 2:1)

| Organism | CAZ | CAZ + PFOB | CAZ + YOB | CAZ + U | CAZ + XOB |
|---|---|---|---|---|---|
| *E. cloacae* P99 | 32 | 4 | 8 | 4 | 8 |
| *E. cloacae* Hennessy | >64 | 4 | 8 | 8 | 8 |
| *E. cloacae* 84-CON | >64 | 4 | 16 | 16 | 16 |
| *C. freundii* C2-con | 64 | 2 | 2 | 4 | 4 |
| *S marcescens* S2-con | 1 | 0.5 | 1 | 0.5 | 0.5 |

Once again PFOB, an embodiment of the invention, shows remarkable activity when compared to U (a structurally and stereochemically close composition which is not a zwitterion). This is demonstrated by comparison of the MIC values against *E. cloacae* Hennessy, *E. cloacae* 84-con and *C Freundii* C2-con for PFOB (4,4 and 2, respectively) with those for U (8, 16 and 4). It is also noted that the MIC value for YOB against *C. freundii* C2-con is superior to that of XOB.

SUMMARY

It can be seen that the compositions embodying the invention have a remarkable combination of superior bioavailability combined with "broad spectrum" activity against both class A and C β-lactamases.

There is no simple prediction of dependence or relationship between activity of the compound and the stereochemistry of the substituent at C-6: U and PFOB have the (1'R)-1-hydroxyethyl side chain while XOB and YOB have the (1'S)-1-hydroxyethyl side chain. The superior activities of PFOB and YOB could not have been predicted.

C.1 Chemical Stability of XOB and YOB

The half-lives of hydrolysis were determined at 37° C. in physiological phosphate buffer pH 7.4 by UV spectroscopy at 265 nm at a $10^{-4}$M concentration of oxapenem

| | XOB | YOB |
|---|---|---|
| Half-live of hydrolysis | 6.5 h | 7.0 h |

C.2 Stability of XOB and YOB in Blood Serum

The blood serum stability was determined microbiologically using an agar diffusion test with *Escherichia coli* TEM 1 (penicillin resistant). The oxapenems were incubated with sterile bovine serum (OXOID) at 37° C. in 0.033% concentration. At 0 h, 1.5 h, 3 h, 4.5 h and 6 h intervals aliquot samples (30 ml) were spotted on commercial filter disk (OXOID) containing piperacillin (75 mg) and the remaining amounts of active β-lactamase inhibitor (oxapenem) were calculated from the observed decreasing inhibition diameters (27-12 mm) in comparison with those obtained (24-0 mm) obtained with piperacillin (75 mg) disks spotting various amounts (10 mg, 5 mg, 2.5 mg, 1.25 mg, 0 mg) of β-lactamase inhibitor.

| | XOB | YOB |
|---|---|---|
| Serum half life at 37° C. | 1.0 h | 2.4 h |

Thus, the zwitterionic compound YOB is far more stable than XOB in blood serum, whereas, in contrast, the chemical stability of the two compounds are practically equal. This surprising increase of stability in blood serum of the zwitterionic oxapenem YOB (when compared to XOB, a structurally and stereochemically close composition which is not a zwitterion) is most significant and important. This stability gives high blood levels and long biological half-life and hence a superior ability for treating bacterial infections in human and veterinary therapy.

D. Synthesis of Compound PFOB, A, E, and YOB

D.1 Synthesis of (5R,6R,1'R)-3-(4-amino-1,1-dimethylbutyl)-6-(1'-hydroxyethyl)-7-oxo-4-oxa-1-azabicyclo[3.2.0]hept-2-ene-2-carboxylic Acid [PFOB]

The synthesis described below is shown schematically in FIG. 2 of the attached drawings.

To a 35 L Pfaudler vessel (GLMS) was charged acetonitrile (16.7 kg) and (3R,4R)-4-(acetoxy)-3-[(1R)-1-[[(1,1-dimethylethyl)dimethylsilyl]oxy]ethyl]-2-azetidinone (3.34 kg, 11.6 moles). To the header flask was charged 21% sodium methyl mercaptan (5.8 L, 17.4 moles, 1.5 equivalents). This was added to the batch at 15-20° C. (cooling required to control exotherm) over two hours. The batch was then stirred for 1 hour after which time TLC analysis showed completion. The lower aqueous phase was discharged and the product (acetonitrile) phase washed with 6.7 L 20% brine prior to being stripped to dryness on a rotary evaporator (20 L). The crude product was then crystallised from hexane (13.3 L) cooling to 0° C. from reflux. The crystalline product was filtered and washed with hexane (1 L). Vacuum drying afforded compound III of FIG. 2 (2.49 kg, 78%) m.p. 93° C. as white needles.

To a 20 L vessel (glass) was charged THF (8.25 L) followed by compound (III) (1.65 kg, 6.0 moles). The batch was cooled to −40° C. and 2.5 M butyl lithium (2.4 L) charged at <−25° C. (typically −45 to −35° C.), over 1 hour. This was allowed to come to −25° C. To a second vessel was charged THF (4.1 L) and para-nitrobenzyl iodoacetate (1.92 kg, 6.02 moles,) which was then cooled to −10° C. The solution of compound (III) was then to transferred to the second solution whilst maintaining temperature <0° C. (typically <−8° C.), over 30 minutes using cannula under vacuum. After stirring to completion (two hours at <−5° C.) the batch was cooled to −10° C. and added to a 50 L vessel containing 20% brine (16 L). The lower aqueous phase was back extracted with dichloromethane (13 L). The two organic phases were then combined and stripped to dryness to afford crude compound (IV) of FIG. 2 (approx 3 kg). THF was charged (approx 2 L) to enable storage of the product as an approx 40% solution.

A THF solution (3.54 L) containing approximately 40% compound IV, (1292 g, 2.76 moles) is stripped to KF<0.1% then redissolved in fresh THF (KF<0.05%), 7.5 L. To this was added 5-azido-2,2-dimethylpentanoic acid chloride (1.23 kg, 6.5 moles, 2.35 equivalents) at <−50° C. A 20% (1.04 M) solution of lithium bis(trimethylsilyl)amide is added (6000 ml, 6.24 moles, 2.25 equivalents) dropwise at <−65° C. The mixture darkened considerably and was left to stir at −70° C. for 1 hour. The reaction was quenched by charging onto toluene (12.5 L) and 10% HCl (12.5 L). The organic phase was then washed successively with 25% $KHCO_3$ (12.5 L) water (12.5 L) and saturated brine (6 L). The organic phase was then concentrated and evaporated to afford a dark concentrated solution (approx 30% product).

To 25 kg of flash silica made up with approx 50 L toluene was charged material (from three batches of the above reaction) dissolved in 20% hexane in toluene (20 L). This was eluted under 0.5 bar pressure to load the material onto the column and recycled until fronts began to appear (Fraction 1). A small amount of fronts was separated in this fraction and discarded. The following fractions were then eluted;

| | |
|---|---|
| Fractions 2–4 | Toluene (25 L each) |
| Fractions 5–6 | 6% Ethyl Acetate in Toluene (25 L each) |
| Fractions 7–8 | 8% Ethyl Acetate in Toluene (25 L each) |
| Fractions 9–10 | 10% Ethyl Acetate in Toluene (25 L each) |

Figure 2:
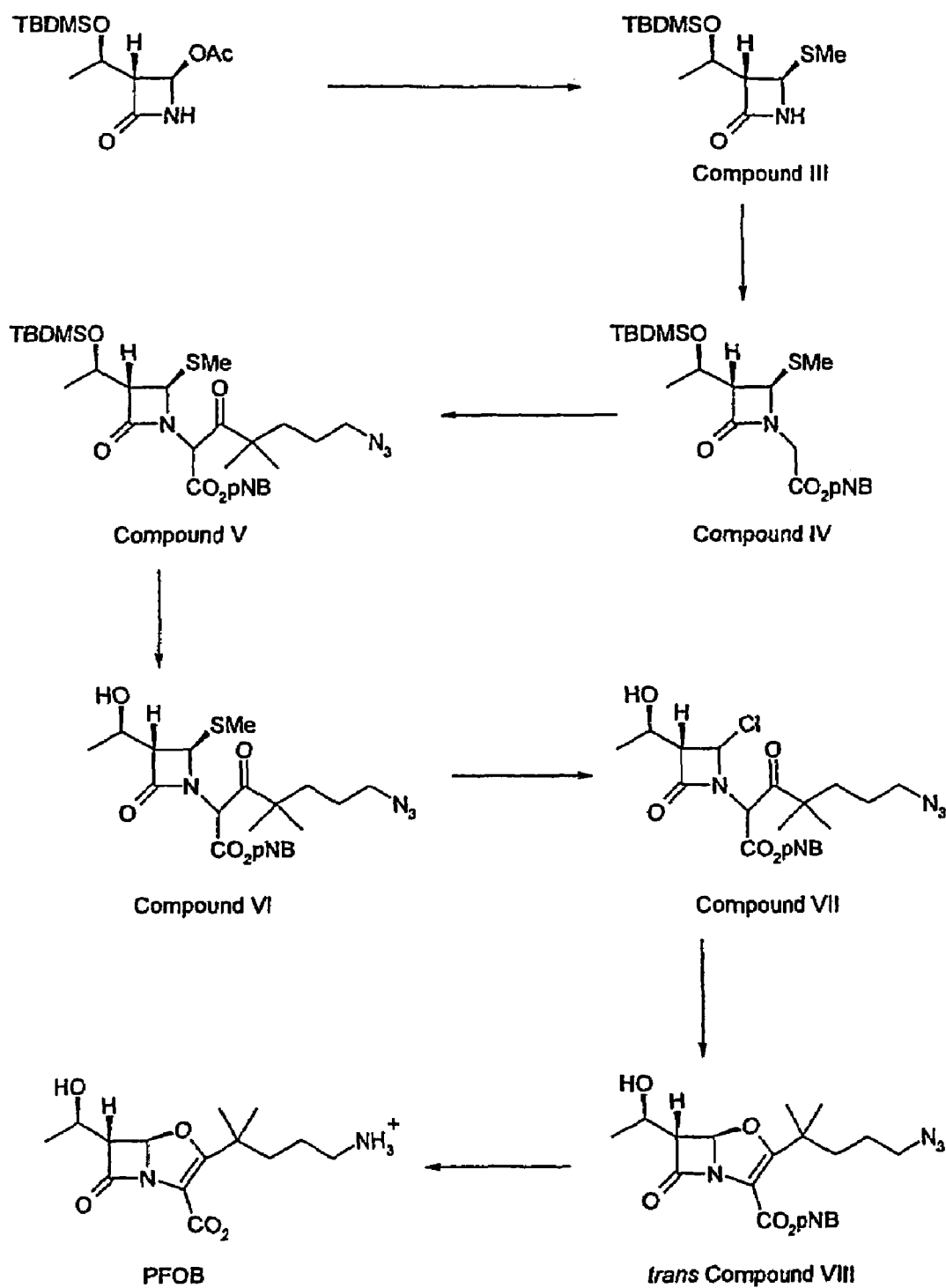
FIG. 2 shows schematic diagram of the synthesis of a compound embodying the invention (PFOB) from a commercially available compound.

The fractions containing product were then stripped to a volume of 25 L of a 13.5% solution of compound V of FIG. 2 (3.51 kg, 68%)

A tetrahydrofuran solution of compound V was stripped on a rotary evaporator until an oil (4.44 kg, containing 3.2 kg compound V, 5.15 mol, including some THF). This oil was re-dissolved in THF (10.75 L) to form a final solution (KF 0.0326%). This was charged to the 100 L vessel, followed by acetic acid (2.98 L) and tetra-n-butyl-ammonium fluoride (5.36 kg, 17.13 mol) and more THF (21.5 L). This was accompanied by some foaming during charging. The batch was heated until at reflux (65° C.) and then held at close to reflux for 16 hours. Sampling for TLC analysis showed only a trace amount of starting material. Toluene (32 L) was added and the vessel contents were cooled to 20° C., prior to quench with 1M. potassium bicarbonate solution (27 L) over 15 minutes with frothing again.

The organic phase was washed with 1M potassium bicarbonate solution (2×27 L), 10% brine (4×11 L) and 20% brine solution (3 L). This washing regime was to ensure the thorough removal of acetic acid.

The toluene solution was stripped to a volume of approximately 5 L and stored in a freezer whilst a second batch was prepared giving a further 4.2 kg of crude product. The crude material was purified by dry flash column chromatography using nitrogen pressure (0.5 bar).

To a 30 cm diameter column was charged a slurry of flash silica (Chrogel Silica 1254, 25 kg) in toluene (50 L), giving a bed depth of 80 cm after settling. The toluene was eluted until the silica was partially dry. The crude product from above (8.5 kg) was dissolved in toluene (20 L) and charged to the silica and loaded onto the column using nitrogen pressure. The product was then eluted with the following solvent mixtures.

| | |
|---|---|
| 100% toluene | 50 L |
| toluene:ethyl acetate (98:2) | 75 L |
| toluene:ethyl acetate (95:5) | 25 L |
| toluene:ethyl acetate (80:20) | 100 L |
| toluene:ethyl acetate (70:30) | 50 L |
| toluene:ethyl acetate (60:40) | 50 L |
| toluene:ethyl acetate (60:40) + 0.5% isopropanol | 50 L |

The following fraction sizes were collected—

| Fraction Number | Fraction Size |
|---|---|
| 1–7 | 25 L |
| 8–12 | 5 L |
| 13–20 | 25 L |

Concentration in vacuo on a 20 L rotary evaporator afforded compound VI of FIG. 2 as a pale red-orange oil, (single spot by TLC, 4.004 kg, 7.88 mol, 76.5%).

To a 2 L flask was charged dichloromethane (1.02 L) and methyl disulphide (398 g, 4.23 mol). A radical scavenger (3-tert-butyl-4-hydroxy-5-methylphenylsulphide, 1.85 g, 0.005 mol) was then charged and the batch cooled to −35° C. Chlorine gas (296 g, 8.35 mol) was sparged into the solution over 2 hours, resulting in an orange solution of the methyl sulphenyl chloride.

This solution was added to a 20 L flask containing dichloromethane (11.4 L) and compound VI (4.97 kg of a 38.2% solution in dichloromethane, 1.9 kg active, 3.74 mol) at −25° C. to −15° C. over 25 minutes. The batch was then stirred at −25° C. for 20 minutes. When the reaction was complete, as indicated by TLC (absence of starting material), the batch was quenched in a 50 L flask containing a solution of sodium. hydrogen sulphite (1.196 kg) and sodium hydrogen carbonate (0.975 kg) in water (23 L). The phases were separated and the aqueous phase back-extracted with dichloromethane (1.5 kg, 2 L). The combined organic phases were washed with saturated brine solution (6 L) and dried over magnesium sulphate (1 kg) before concentration in vacuo to an oil on a 20 L rotary evaporator to yield compound VII of FIG. 2 as a crude red oil (1.74 kg, 3.51 mol, 93.7% crude yield) which was dissolved in tetrahydrofuran (2.71 kg) and stored at −30° C. for use in the next stage.

Compound VII (1.028 kg) was concentrated in vacuo leaving a crude oil, which was dissolved in tetrahydrofuran (9.5 kg, 10.6 L, KF value=0.02%) an d charged to a 20 L flask. The flask was then cooled back to <−50° C. and triethylamine (848 g, 1.168 L) added over 5 minutes. The batch was stirred at −50° C. for 1 hour, warmed to 20° C. over two hours and then stirred at 20-25° C. for another 2 hours. The reaction was shown to be complete by TLC (disappearance of starting material). Toluene (17.7 L) was charged to a 50 L flask and the reaction mixture added to this, followed by a rinse with toluene (3.55 L). After settling and splitting, the organic phase was washed with 10% brine solution (3×12 L), followed by saturated brine solution (3 L), dried over sodium sulphate (1 kg) before and concentrated in vacuo until a 2 L volume of solution of compound VIII of FIG. 2 in toluene was obtained which was made up to 4.5 kg with toluene.

A slurry of silica gel 60 (1500 g) in diethyl ether: n-pentane (1.5:1) was made up and charged to a jacketed column (80 mm i.d.) and cooled by glycol circulating at −15° C. Crude compound VIII (22.5-25.0% w/w, 450 g solution, 101.3-112.5 g active crude mixture) was charged to the silica and eluted with diethyl ether:n-pentane (1.5:1) pre-cooled to −20° C. The product was eluted with 25 L of mixed solvent and 2 L of diethyl ether with collection of 1 L fractions and concentrated in vacuo at −20° C. to give trans compound VIII of FIG. 2 (typically 46 g) which was stored at −20° C.

To a 10 L flask was charged demineralised water (750 ml), 10% palladium on charcoal (Johnson Matthey, Type 87 L, 60% water, 55 g damp solid, 2.2 g palladium, 0.0207 mol, 0.0211 equiv) and ethyl acetate (1750 ml). The flask was purged with nitrogen for 15 minutes then hydrogen and the batch cooled to <0° C. Vigorous agitation (450 to 500 rpm) was used throughout.

Trans compound VIII (45 g, 0.098 mol) was dissolved in ethyl acetate (300 ml) at −30° C., resulting in a final solution temperature of −5° C. This was added to the batch whilst maintaining the reaction and header temperatures at <0° C.

The batch was hydrogenated for up to 90 minutes, maintaining a steady hydrogen flow throughout. The reaction was deemed complete when HPLC analysis of the organic layer showed an absence of starting material.

The catalyst was removed by filtration through Celite 521 (50 g, pre-washed with demineralised water and ethyl acetate) as quickly as possible maintaining a temperature of less than 0° C. The spent catalyst was washed with pre-cooled ethyl acetate (100 ml) and demineralised water (2×100 ml) at 0° C. After settling, the aqueous phase was isolated, held at 0° C. and washed with n-pentane:toluene (3:1) (225 ml) which had been cooled to −20° C.

The aqueous phase containing product was successively filtered through 1.6 mm glass fibre paper (GF/A grade) and polyethersulphone membrane (pore size 0.2 mm, PES grade) with a glass fibre pre-filter cartridge (GFP grade) resulting in a completely clear pale yellow-amber solution. This was was frozen in 200 ml aliquots onto the walls of 500 ml flasks at −78° C. After freeze-drying for 72 hours (5R,6R,1'R)-3-(4-amino-1,1-dimethylbutyl)-6-(1'-hydroxyethyl)-7-oxo-4-oxa-1-azabicyclo[3.2.0]hept-2-ene-2-carboxylic acid (typically ~50% corrected yield) was isolated as a voluminous off-white to pale yellow solid.

D.2 Synthesis of A, E

Compounds A and E are made by simple adaptation of the synthesis of PFOB, above.

D.3 Synthesis of (5R,6R,1'S)-3-(4-amino-1, 1-dimethylbutyl)-6-(1-hydroxyethyl)-7-oxo-4-oxa-1-azabicyclo[3.2.0]hept-2-ene-2-carboxylic Acid [YOB]

In a 500 ml Schlenk flask fitted with a magnetic stirrer and a reflux condenser connected with a balloon filled with nitrogen a solution of p-nitrobenzyl (3S,4R)-(3-(1'(R)-tert-butyldimethylsilyloxyethyl)-4-methylthio-2-oxoazetidinyl) acetate (14.13 g, 30.15 mmol) [Compound IV in the synthesis of PFOB.], acetic acid (17.3 ml, 302 mmol) and tetrabutylammonium fluoride (23.2 g, 88.6 mmol) in dry tetrahydrofuran was refluxed for 12 h. Tlc on silica gel indicated an almost complete conversion. The mixture was diluted with toluene (2500 ml) and washed subsequently with 500 ml portions of 10% KHCO₃, 10% NaCl (twice) and saturated NaCl. The organic phase was dried over magnesium sulfate, filtered and the filtrate evaporated in vacuum leaving a noncrystalline residue (12 g) Purification by column chromatography on silica gel (440 g, 40-63 mm) with toluene-ethyl acetate (2:1, 3:2, and 1:1) using 440 ml fractions gave p-nitrobenzyl (3S,4R)-(3-(1'(R)-hydroxyethyl)-4-methylthio-2-oxoazetidinyl) acetate as a pure crystalline product (6.38 g, 60%) from fractions 10-16. Mp. 77-79° C.

To a 500 ml Schlenk flask fitted with a magnetic stirrer, a rubber septum and a balloon filled with nitrogen p-nitrobenzyl (3S,4R)-(3-(1'(R)-hydroxyethyl)-4-methylthio-2-oxoazetidinyl)acetate (6.35 g, 17.93 mmol), triphenylphosphine (9.4 g, 35.86 mmol) and dry tetrahydrofuran (134 ml) were added. To this mixture dry formic acid (2.03 ml, 53.79 mmol) was added and to this stirred solution at −10° C. diisopropyl azodicarboxylate (7.03 ml, 35.86 mmol) was slowly added over 30 min. A precipitate was formed after 10 min. The suspension was stirred for additional 30 min at 0° C. and for additional 90 min at room temperature where upon the precipitate redissolved. A dark yellow solution was thus obtained. The reaction mixture was diluted with toluene (1500 ml) and subsequently washed with 1200 ml portions of water, 10% KHCO₃, and 10% NaCl. The organic layer was dried over magnesium sulfate, filtered and the solvent removed in vacuum leaving an oil. It was purified by silica gel chromatography (205 g, 63-200 mm) using 200 ml fractions of toluene-ethyl acetate (9:1). The fractions were investigated by silica gel tlc (chloroform-ethyl acetate 4:1). From fractions 6-15 p-nitrobenzyl (3S,4R)-(3-(1'(S)-formyloxyethyl)-4-methylthio-2-oxoazetidinyl) acetate was collected as an impure semi crystalline solid (10.01 g) (6.85%=100%).

To a 500 ml round bottomed flask fitted with a magnetic stirrer crude p-nitrobenzyl (3S,4R)-(3-(1'(S)-formyloxyethyl)-4-methylthio-2-oxoazetidinyl) acetate (10.01 g, prepared from 17.93 mmol of precursor) and methanol (180 ml) were added. To this mixture aqueous 1 N HCl (17.9 ml, 17.9 mmol) was added and the solution stirred overnight at room temperature. Tlc on silica gel indicated complete reaction. The reaction mixture was diluted with toluene (1600 ml) and the solution washed subsequently with cold water (1100 ml), 10% KHCO₃ (500 ml) and 10% NaCl (500 ml). The organic layer was dried over magnesium sulfate, filtered and the resulting solution evaporated in vacuum leaving an oil. It was purified by column chromatography on silica gel using 200 ml fractions and toluene-ethyl acetate (2:1 and 1:1). p-Nitrobenzyl (3S,4R)-(3-(1' (S)-hydroxyethyl)-4-methylthio-2-oxoazetidinyl) acetate was obtained as a noncrystalline solid (3.77 g, 59%) from fractions 9-19.

To a 100 ml Schlenk flask fitted with a magnetic stirrer and a balloon filled with nitrogen p-nitrobenzyl (3S,4R)-(3-(1'(S)-hydroxyethyl)-4-methylthio-2-oxoazetidinyl)acetate (3.72 g, 10.50 mmol) and dry (ethanol free) methylene chloride (23 ml) were added. A solution of p-nitrobenzyl chloroformate (3.08 g, 14.28 mmol) in methylene chloride was slowly added at −18° C. To this mixture was added with stirring solid N,N-dimethylaminopydridine (1.74 g, 14.28 mmol) in small portions over 20 min. After stirring at −18° C. for 4 h silica gel tlc indicated a complete reaction. The reaction mixture was diluted with methylene chloride (230 ml) and the resulting solution was washed subsequently with portions (120 ml) of 1 N HCl, saturated NaHCO₃ and 10% NaCl. The HCl phase was reextracted with methylene chloride (40 ml) and the extraction solution washed with NaHCO₃. The combined extraction solutions were dried over magnesium sulfate, filtered and the solvent removed in vacuum leaving the crude product (5.24 g). Purification by silica gel chromatography (170 g, 63-200 mm) using 170 ml fractions of toluene-ethyl acetate (6:1) yielded p-nitrobenzyl (3S,4R)-(3-(1'(S)-p-nitrobenzyloxycarbonyloxyethyl)-4-methylthio-2-oxoazetidinyl)acetate as a noncrystalline solid (4.80 g, 86

To a 250 ml Schlenk flask fitted with a magnetic stirrer, a rubber septum and a balloon filled with nitrogen p-nitrobenzyl (3S,4R)-(3-(1'(S)-p-nitrobenzyloxycarbonyloxyethyl)-4-methylthio-2-oxoazetidinyl)acetate (1.00 g, 1.87 mmol) and dry tetrahydrofuran (46 ml) were added. To this mixture 5-azido-2,2-dimethyl-pentanoyl chloride (0.37 g, 1.96 mmol) was added at −78° C. and subsequently at −78° C. a 1 M solution of lithium bis-trimethylsilylamide (3.74 ml, 3.74 mmol) in tetrahydrofuran was added within 15 min. The initially formed orange solution turned to pale yellow. After 15 min of additional stirring tlc on silica gel indicated complete reaction. The reaction mixture was diluted with toluene (240 ml), washed with portions (220 ml) of 2 N HCl and twice with saturated NaCl. The organic phase was dried over magnesium sulfate, filtered and the filtrate evaporated in vacuum to give noncrystalline crude material (1.38 g) after short drying in high vacuum. Purification by column chromatography on silica gel (92 g, 63-200 mm) with toluene-ethyl acetate (9:1) using 90 ml fractions gave p-nitrobenzyl 7-azido-4,4-dimethyl-2-[(3S,4R)-4-methylthio-3-[(S)-1-p-nitrobenzyloxcarbonyloxyethyl]-2-oxo-1-azetidinyl]-3-oxo-heptanoate as a pale yellow noncrystalline solid (1.01 g, 79%) after double evaporation with methylene chloride and drying in high vacuum.

To a 250 ml Schlenk flask fitted with a magnetic stirrer, a rubber septum and a balloon filled with nitrogen p-nitrobenzyl 7-azido-4,4-dimethyl-2-[(3S,4R)-4-methylthio-3-[(S)-1-p-nitrobenzyloxcarbonyloxyethyl]-2-oxo-1-azetidinyl]-3-oxoheptanoate (0.97 g, 1.41 mmol) and dry, ethanol free methylene chloride (56 ml) were added. To this mixture at −60° C. dry chlorine gas was introduced by a syringe, by inlet through the surface. After 10 min at −50° C. tlc on silica gel indicated complete reaction. The cold solution was poured on an aqueous solution containing $NaHSO_3$ (2.82 g, anhydrous) and sodium carbonate (2.23 g, anhydrous). The mixture was shaken for 4 min, the organic phase collected and the aqueous phase extracted with a small portion of methylene chloride. The organic solutions were subsequently washed twice with portions (37 ml) of 10% NaCl and the organic solutions were combined and dried over magnesium sulfate. After evaporation in vacuum a noncrystalline solid (0.95 g) resulted. It was purified by fast column chromatography on silica gel (2.3 g, 63-200 mm) with toluene-ethyl acetate 19:1 and 4:1 using 5 ml fractions. From fractions 2-14 p-nitrobenzyl 7-azido-2-[(3S,4R)-4-chloro-3-[(S)-1-p-nitrobenzyloxcarbonyloxyethyl]-2-oxo-1-azetidinyl]-4,4-dimethyl-3-oxo-heptanoate was obtained as a pale yellow, non-crystalline solid (930 mg, 97%) after evaporation of the solvent in vacuum and drying of the residue in high vacuum.

To a 100 ml Schlenk flask fitted with a magnetic stirrer, a rubber septum and a balloon filled with nitrogen p-nitrobenzyl 7-azido-[(3S,4R)-4-chloro-3-[(S)-1-p-nitrobenzyloxcarbonyloxyethyl]-2-oxo-1-azetidinyl]-4,4-dimethyl-3-oxo-heptanoate (910 mg, 1.35 mmol) and dry tetrahydrofuran (27 ml) were added. To this mixture a 0.92 M solution of potassium tert-butoxide (1.54 ml, 1.42 mmol) in dry tert-butanol was added slowly at −30° C. The reaction mixture was allowed to stir for 150 min at −30° C. Tlc indicated a complete conversion. The dark yellow solution was diluted with ethyl acetate (150 ml), allowed to stand for 5 min and then was washed with. 10% NaCl (130 ml), 10% NaCl (65 ml) and saturated NaCl (65 ml). The organic layer was collected and dried over magnesium sulfate. After filtration and evaporation of the solvent in vacuum a yellow oil (860 mg) resulted after drying at high vacuum for 90 min. It was purified by medium pressure column chromatography at low temperature (−13° C.) on silica gel (60 g, 5-20 mm) with toluene-butyl acetate (19:1) collecting fractions of 30 ml each. The fractions were kept at −20° C. From fractions 11-13 pure trans p-nitrobenzyl (5R,6R)-3-[4-azido-1,1-dimethylbutyl]-6-[(S)-1-p-nitrobenzyloxycarbonyloxyethyl]-7-oxo-4-oxa-1-azabicyclo[3.2.0]hept-2-ene-2-carboxylate (306 mg, 35%) was obtained as a colourless non-crystalline solid after evaporation of the solvent in high vacuum. From fractions 14-21 a cis-trans isomeric mixture (277 mg, 32%) was secured similarly.

In a 100 ml two necked flask fitted with a magnetic stirrer, a rubber septum and connected to a hydrogenation apparatus palladium on carbon catalyst (10%, 300 mg) in ethyl acetate (13 ml) and water (13 ml) was prehydrogenated for 20 min at 0° C. A solution of p-nitrobenzyl (5R,6R)-3-[4-azido-1,1-dimethylbutyl]-6-[(S)-1-p-nitrobenzyloxycarbonyloxyethyl]-7-oxo-4-oxa-1-azabicyclo[3.2.0]hept-2-ene-2-carboxylate (280 mg, 0.44 mmol) in ethyl acetate (10 ml) was then added with a syringe at 0° C. with stirring. After 50 min of stirring at 0° C. hydrogen uptake came to an end (90 ml of hydrogen was consumed). The catalyst was removed by filtration, washed with a small portion of ethyl acetate and water and the chilled two phase mixture allowed to separate. The aqueous phase was washed twice with portions (3 ml) of cold ethyl acetate and water and the ethyl acetate phases were reextracted twice with portions (3 ml) of water. Residual ethyl acetate was removed from the combined water phases in vacuum and then in high vacuum at 0° C. and the volume was reduced to 13 ml in high vacuum. The solution was lyophilized at −25° C. for three days to give (5R,6R)-3-[4-amino-1,1-dimethylbutyl]-6-[(S)-1-hydroxyethyl]-7-oxo-4-oxa-1-azabicyclo[3.2.0]hept-2-ene-2-carboxylic acid (YOB) as a colourless voluminous powder (98 mg, 75%)

E. Preparations for Use as Pharmaceuticals

Pharmaceutical preparations may be prepared as follows.

EXAMPLE 1

(Method A)

A highly stable pharmaceutical preparation of (5R,6R,1'R)-3-(4-amino-1,1-dimethylbutyl)-6-(1'-hydroxyethyl)-7-oxo-4-oxa-1-azabicyclo[3.2.0]hept-2-ene-2-carboxylic acid (PFOB) in lactose.

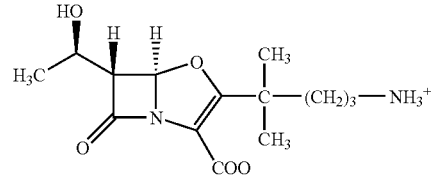

A solution of 3.79 g (8.25 mmol) p-nitrobenzyl(5R,6R,1'R)3-(4-azido-1-dimethylbutyl)-6-(1'-hydroxyethyl)-7-oxo-4-oxa-1-azabicyclo[3.2.0]hept-2-ene-2-carboxylate in 30 ml ethyl acetate was added at 0° via a syringe through a rubber septum to a prehydrogenated mixture of 3.1 g palladium on charcoal (10%) in 120 ml of ethyl acetate and 60 ml of water. After a reaction time of 70 minutes at 0° C., 840 ml of hydrogen have been taken up (theoretical amount 740 ml). The reaction mixture was filtered through a G5 glass filter of 10 cm diameter, the residue washed with 30 ml of cold water and 30 mol of cold ethyl acetate and the ethyl acetate layer removed from the combined filtrates. The aqueous layer was washed at 0° C. with 50 ml of cold ethyl acetate and 50 ml of cold toluene and the resulting aqueous colloidal solution pressed through a membrane filter using a syringe where upon the layers separated. The aqueous layer was evacuated in high vacuum in order to remove residual organic solvents. To the aqueous solution (89.8 ml) a cold solution containing 7.20 g lactose monohydrate in 180 ml water was added and 3 ml portions of the resulting solution filled into glass ampoules. The-content was frozen in a dry ice-acetone bath and the water removed in a lyophiliser at −25° C. during 4 days at 0.01 mbar. The resulting white powder was dried in a desiccator over phosphorus pentoxide overnight at 0.001 mbar and room temperature leaving 98.3 mg of white powder in each ampoule. UV spectroscopy in water at 262 nm revealed a content of 18.2 mg of title compound and 80.1 mg of lactose in each ampoule. The ampoules were filled with dry nitrogen and sealed or alternatively stored over drying agents.

A pharmaceutical composition may also be prepared as follows:

EXAMPLE 2

(5R,6R,1'R)-3-(4-amino-1,1-dimethylbutyl)-6-(1'-hydroxyethyl)-7-oxo-4-oxa-1-azabicyclo[3.2.0]hept-2-ene-2-carboxylic acid. (PFOB)

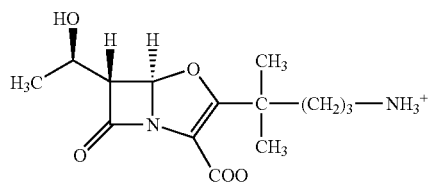

Following the procedure given in section C1 neat title compound as a white powder was obtained after simple lyophilization at −25° C. (without lactose) and after overnight drying at 0.001 bar and room temperature over phosphorus pentoxide. The compound thus obtained is suitable for administration as a pharmaceutical by known methods, or those discussed below.

EXAMPLE 3

Production of pharmaceutical preparations.

The novel oxapenem compounds may be used in pharmaceutical compositions. The oxapenem compounds may be made into pharmacutical compositions/medicaments by conventional methods, such as those disclosed in EP 0 301394. Other methods of making medicaments include the following:

A unit dose form is prepared by mixing 300 mg of the (4:1) co-lyophilizate of lactose monohydrate and (5R,6R,1'R)-3-(4-amino-1,1-dimethylbutyl)-6-(1'-hydroxyethyl)-7-oxo-4-oxa-1-azabicyclo[3.2.0]hept-2-ene-2-carboxylic acid (PFOB, Example 1) with 120 mg of cefaclor and 5 mg of magnesium stearate and the 425 mg mixture is added to a gelatine No.3 capsule. Similarly, if co-Lyophilisate of a higher content of oxapenem-3-carboxylic acid is used, other dose forms may be prepared likewise and filled into No.3 gelatin capsules; and should it be necessary to mix more than 425 mg of constituents together, larger capsules, and also compressed tablets and pills, may also be produced. The following examples illustrate the production of pharmaceutical preparations.

TABLE 5

| | |
|---|---|
| (4:1) co-lyophilisate of lactose monohydrate and (5R,6R,1'R)-3-(4-amino-1,1-dimethylbuty)-6-(1'-hydroxyethyl)-7-oxo-4-oxa-1-azabicyclo[3.2.0]hept-2-ene-2-carboxylic acid | 625 mg |
| Cefaclor | 250 mg |
| Maize starch V.S.P. | 200 mg |
| Dicalcium phosphate | 60 mg |
| Magnesium stearate | 60 mg |

The co-lyophilisate and the other active constituent (Ceflacor) are mixed with the dicalcium phosphate and about half of the maize starch. The mixture is then granulated and coarsely sieved. It is dried at 45° C. and resieved through sieves of mesh width 1.0 mm (No. 16 screens). The remainder of the maize starch and the magnesium stearate are added and the mixture is compressed to form tablets each weighing 1195 mg and having a diameter of 1.27 cm (0.5 in.).

Parenteral Solution

| Ampoule | |
|---|---|
| (4:1) co-lyophilisate of lactose monohydrate and (5R,6R,1'R)-3-(4-amino-1,1-dimethylbutyl)-6-(1'-hydroxyethyl)-7-oxo-4-oxa-1-azabicyclo[3.2.0]hept-2-ene-2-carboxylic acid | 1250 mg |
| Ceftazidime | 500 mg |
| Sterile water (is added from a separate ampoule using a syringe immediately before use) | 5 ml |

Opthalmic Solution

| | |
|---|---|
| (4:1) co-lyophilisate of lactose monohydrate and (5R,6R,1'R)-3-(4-amino-1,1-dimethylbutyl)-6-(1'-hydroxyethyl)-7-oxo-4-oxa-1-azabicyclo[3.2.0]hept-2-ene-2-carboxylic acid | 625 mg |
| Ceftazidime | 250 mg |
| Hydroxypropylmethylcellulose | 15 mg |
| Sterile water (is added from a separate ampoule using a syringe immediately before use | 2 ml |

Optic Solution

| | |
|---|---|
| (4:1) co-lyophilisate of lactose monohydrate and (5R,6R,1'R)-3-(4-amino-1,1-dimethylbutyl)-6-(1'-hydroxyethyl)-7-oxo-4-oxa-1-azabicyclo[3.2.0]hept-2-ene-2-carboxylic acid | 250 mg |
| Ceftazidime | 100 mg |
| Benzalkonium chloride | 0.1 mg |
| Sterile water (is added from a separate ampoule using a syringe immediately before use) | 2 ml |

Topical Cream or Ointment

| | |
|---|---|
| (4:1) co-lyophilisate of lactose monohydrate and (5R,6R,1'R)-3-(4-amino-1,1-dimethylbutyl)-6-(1'-hydroxyethyl)-7-oxo-4-oxa-1-azabicyclo]3.2.0]hept-2-ene-2-carboxylic acid | 250 mg |
| Ceftazidime | 100 mg |
| Polyethylene glycol 4000 V.S.P. | 800 mg |
| Polyethylene glycol 400 V.S.P. | 200 mg |

YOB, A, B, D and E may be used as pharmaceutically active agents in similar examples by simply substition for PFOB in the above formulations.

It should be noted that it is not necessary to co-lyophilise the active oxapenem (PFOB, YOB etc) with carrier (e.g. lactose) before mixing with the other reagents, although co-lyophilisation should enhance stability.

The active components in the above preparations can be mixed alone or together with other biologically active components, such as lincomycin, a penicillin, streptomycin, novobiocin, gentamycin, neomycin, colistin and klanamycin, or with other therapeutic agents such as probenicid.

It is understood that the specification and examples are illustrative but not limitative of the present invention and that other embodiments within the spirit on a scope of the invention will suggest themselves to those skilled in the art.

The invention claimed is:

1. An oxapenem compound represented by the formula:

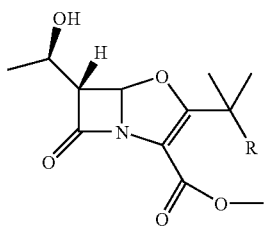

wherein R is $-(CH_2)_n-NH_3^+$ and n is 3-8.

2. An oxapenem compound according to claim 1, wherein n is 3 or 4.

3. An oxapenem compound according to claim 1, wherein R is $-(CH_2)_3NH_3^+$.

4. A pharmaceutical composition comprising a pharmacologically effective amount of an oxapenem compound according to claim 1 and a carrier.

5. A β-lactamase inhibitor comprising an oxapenem compound according to claim 1 and a carrier.

6. A pharmaceutical composition according to claim 4 which further comprises a pharmaceutically effective amount of an antibiotic.

7. A method of treatment of bacterial infection comprising a step of administering to a patient in need thereof a pharmacologically effective amount of a compound according to claim 1.

8. A method of treatment according to claim 7 in which R is $-(CH_2)_4NH_3^+$, or $-(CH_2)_3NH_3^+$.

9. A method according to claim 7, which further comprises a step of administering to the patient a pharmacologically effective amount of an antibiotic.

10. An oxapenem compound represented by formula Ia or Ib:

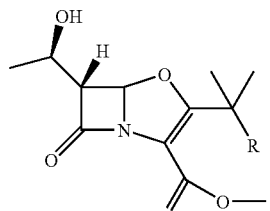

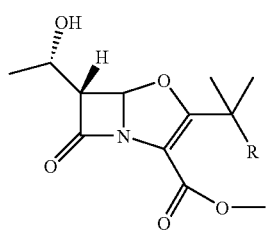

wherein R is a $C_1$-$C_8$ branched or straight chain alkyl group substituted with $-NHCH:NH_2^+$.

11. An oxapenem compound represented by formula Ia or Ib:

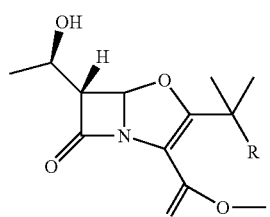

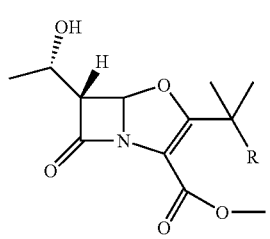

wherein R is $-(CH_2)_nNHCH:NH_2^+$, and n is an integer from 1 to 8.

12. The oxapenem compound of claim 11, wherein the compound is represented by formula Ia and n is 1 or 2.

13. The oxapenem compound of claim 12, wherein n is 1.

14. The oxapenem compound of claim 12, wherein n is 2.

15. An oxapenem compound represented by formula Ia or Ib:

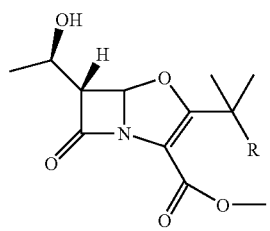

-continued

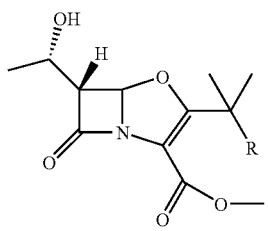

Ib wherein R is —(CH$_2$)$_n$—NH$_3^+$ and n is 4-8.

16. An oxapenem compound according to claim 1, wherein R is —(CH$_2$)$_4$NH$_3^+$.

17. A pharmaceutical composition according to claim 4, wherein the oxapenem compound is represented by the formula:

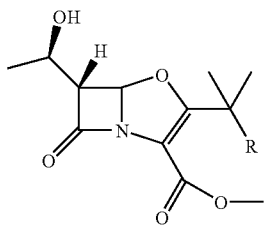

wherein R is —(CH$_2$)$_n$—NH$_3^+$ and n is 3 or 4.

18. A pharmaceutical composition according to claim 17, wherein n is 3.

19. A pharmaceutical composition according to claim 17, wherein n is 4.

20. A pharmaceutical composition according to claim 17 which further comprises a pharmaceutically effective amount of an antibiotic.

21. A pharmaceutical composition according to claim 18 which further comprises a pharmaceutically effective amount of an antibiotic.

22. A pharmaceutical composition according to claim 19 which further comprises a pharmaceutically effective amount of an antibiotic.

23. A method of treatment according to claim 7, wherein the oxapenem compound is represented by the formula:

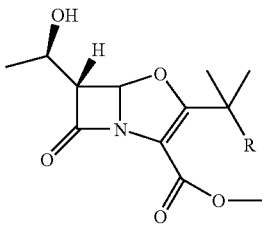

wherein R is —(CH$_2$)$_4$NH$_3^+$.

24. A method of treatment according to claim 7, wherein the oxapenem compound is represented by the formula:

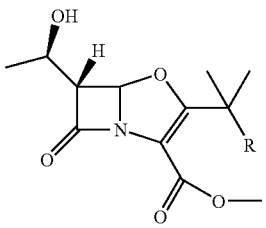

in which R is —(CH$_2$)$_3$NH$_3^+$.

25. A method according to claim 23, which further comprises a step of administering to the patient a pharmacologically effective amount of an antibiotic.

26. A method according to claim 24, which further comprises a step of administering to the patient a pharmacologically effective amount of an antibiotic.

* * * * *